United States Patent [19]

Kummer et al.

[11] 4,080,503
[45] Mar. 21, 1978

[54] 2-AMINO-4-PHENYL-2-IMIDAZOLINES AND SALTS THEREOF

[75] Inventors: Werner Kummer; Herbert Köppe; Helmut Stähle, all of Ingelheim am Rhein; Walter Haarmann, Biberach an der Riss, all of Germany

[73] Assignee: Boehringer Ingelheim GmbH, Ingelheim am Rhein, Germany

[21] Appl. No.: 379,750

[22] Filed: Jul. 16, 1973

[30] Foreign Application Priority Data

Jul. 19, 1972   Germany ............................ 2235314
Jul. 19, 1972   Germany ............................ 2235328

[51] Int. Cl.² ..................................... C07D 405/12
[52] U.S. Cl. ............................. 548/316; 260/268 H; 260/268 PH; 260/268 FT; 260/293.7; 424/248.56; 424/248.53; 424/250; 424/267; 424/273 R; 544/139; 548/315; 548/351
[58] Field of Search .................. 260/309.6; 548/315, 548/316

[56] References Cited

U.S. PATENT DOCUMENTS 3,708,485   1/1973   Stahle et al. ........................ 260/254

OTHER PUBLICATIONS

Matier et al., J. Med. Chem. 16(8), 901–908 (1973).
Matier et al., 163rd ACS National Meeting, Boston, Mass. Abstracts of Papers, p. MEDI 2.

*Primary Examiner*—Natalie Trousof
*Attorney, Agent, or Firm*—Hammond & Littell

[57] ABSTRACT

Compounds of the formula

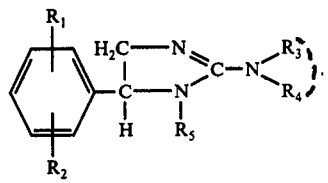

wherein
  $R_1$ and $R_2$, which may be identical to or different from each other, are each hydrogen, chlorine, bromine or alkyl of 1 to 3 carbon atoms,
  $R_3$ is hydrogen, furfuryl, hydroxyethyl, $\beta$-hydroxyphenethyl, monochlorophenyl-ethyl, dichlorophenyl-ethyl, N-ethyl-piperidyl or $-A-NR_6R_7$,
  where
    A is alkylene of 1 to 5 carbon atoms, and
    $R_6$ and $R_7$ are alkyl of 1 to 2 carbon atoms or, together with each other and the nitrogen atom to which they are attached, form a heterocycle selected from the group consisting of pyrrolidino, morpholino, piperazino or N'-dimethyl-phenyl-piperazino,
  $R_4$ is hydrogen or, together with $R_3$ and the nitrogen to which they are attached, forms a heterocycle selected from the group consisting of piperidino, morpholino, dimethyl-morpholino or N'-methyl-piperazino,
  $R_5$ is hydrogen, alkyl of 1 to 3 carbon atoms, hydroxyethyl, diethylamino-ethyl or furfuryl, provided, however, that $R_1$ and $R_2$ are other than both hydrogen or both alkyl at the same time and that $R_3$ and $R_5$ are other than both hydrogen at the same time, or a non-toxic, pharmacologically acceptable acid addition salt thereof; the compounds as well as the salt are useful as hypotensives, platelet aggregation inhibitors and antiarrhythmics.

3 Claims, No Drawings

2-AMINO-4-PHENYL-2-IMIDAZOLINES AND SALTS THEREOF

This invention relates to novel 2-amino-4-phenyl-2-imidazolines and acid addition salts thereof, as well as to methods of preparing these compounds.

More particularly, the present invention relates to a novel class of 2-amino-4-phenyl-2-imidazolines of the formula

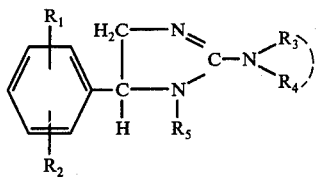

(I)

wherein
$R_1$ and $R_2$, which may be identical to or different from each other, are each hydrogen, chlorine, bromine or alkyl of 1 to 3 carbon atoms,
$R_3$ is hydrogen, furfuryl, hydroxyethyl, β-hydroxyphenethyl, monochlorophenyl-ethyl, dichlorophenylethyl, N-ethyl-piperidyl or —A—$NR_6R_7$, where
  A is alkylene of 1 to 5 carbon atoms, and
  $R_6$ and $R_7$ are alkyl of 1 to 2 carbon atoms or, together with each other and the nitrogen atom to which they are attached, form a heterocycle selected from the group consisting of pyrrolidino, morpholino, piperazino or N'-dimethyl-phenyl-piperazino,
$R_4$ is hydrogen or, together with $R_3$ and the nitrogen to which they are attached, forms a heterocycle selected from the group consisting of piperidino, morpholino, dimethyl-morpholino or N'-methyl-piperazino,
$R_5$ is hydrogen, alkyl of 1 to 3 carbon atoms, hydroxyethyl, diethylamino-ethyl or furfuryl,
provided, however, that $R_1$ and $R_2$ are other than both hydrogen or both alkyl at the same time and that $R_3$ and $R_5$ are other than both hydrogen at the same time, or a non-toxic, pharmacologically acceptable acid addition salt thereof.

The compounds embraced by formula I are cyclic guanidines and may therefore exist in tautomeric forms; they comprise, furthermore, an asymmetric carbon atom, wherefore they may occur as racemates or optical antipodes.

The compounds of the present invention may be prepared by the following methods:

Method A

By reacting an imidazoline of the formula

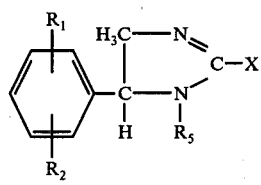

(II)

wherein $R_1$, $R_2$ and $R_5$ have the same meanings as in formula I and X is chlorine, bromine, iodine, lower alkoxy or lower alkyl-mercapto, with an amine of the formula

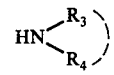

(III)

wherein $R_3$ and $R_4$ have the same meanings as in formula I.

The reaction is preferably performed in the absence of a solvent medium with the reactants in the molten state, but it will also proceed in the presence of an inert solvent medium, such as an alkanol, a ketone or an ether.

Method B

By reacting a phenyl-ethylenediamine of the formula

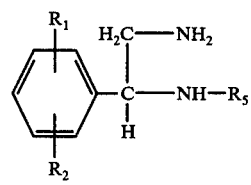

(IV)

wherein $R_1$, $R_2$ and $R_5$ have the same meanings as in formula I, with an amidine derivative of the formula

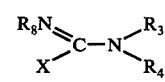

(V)

wherein $R_3$ and $R_4$ have the same meanings as in formula I, X has the same meanings as in formula II, and $R_8$ is hydrogen or alkyl of 1 to 3 carbon atoms.

Method C

By subjecting a compound of the formula

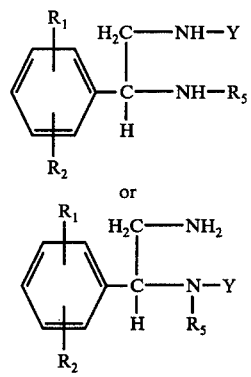

(VI)

or (VIa)

wherein
$R_1$, $R_2$ and $R_5$ have the same meanings as in formula I, and
Y is —C≡N,

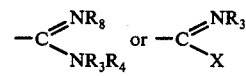

where
$R_3$, $R_4$, $R_8$ and X have the meanings previously defined, to ring closure, preferably in the presence of hexamethylphosphoric triamide.

The starting compounds required for methods A to C are either known compounds or may be prepared by known methods.

For example, a compound of the formula II wherein X is halogen may be prepared by reacting a phenyl-substituted ethylenediamine of the formula IV with a bifunctional carbonic acid derivative, such as phosgene, a chlorocarbonate or an orthocarbonate, to form a correspondingly substituted ethyleneurea, followed by halogenation with an inorganic acid halide, such as phosphorus oxychloride or oxybromide, phosphorus pentachloride or pentabromide, phosphorus trichloride, tribromide or triiodide, or a thionyl halide.

A compound of the formula II wherein X is alkylmercapto may be obtained, for example, by reacting a phenylsubstituted ethylenediamine of the formula IV with carbon disulfide to form a corresponding phenyl-substituted ethylenethiourea, and alkylation of the latter with an alkyl halide or an inorganic acid alkyl ester, such as dimethylsulfate.

A phenyl-substituted ethylenediamine of the formula IV may be prepared by reacting a correspondingly substituted benzaldehyde with ammonium cyanide to form an α-cyano-benzylamine, and hydrogenating the latter.

A compound of the formula VI or VIa may be prepared, for instance by reacting a phenyl-ethylenediamine of the formula IV with an N-substituted alkylmercapto-isothiourea. Some of the compounds of the formula VI or VIa spontaneously cyclize into the corresponding compounds of the formula I at room temperature.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydrofluoric acid, hydroiodic acid, sulfuric acid, phosphoric acid, nitric acid, acetic acid, propionic acid, butyric acid, valeric acid, caproic acid, capric acid, oxalic acid, malonic acid, succinic acid, glutaric acid, maleic acid, fumaric acid, lactic acid, tartaric acid, citric acid, malic acid, gluconic acid, benzoic acid, p-hydroxy-benzoic acid, phthalic acid, cinnamic aid, salicylic acid, ascorbic acid, 8-chloro-theophylline, methanesulfonic acid or the like.

The following examples further illustrate the present invention and will enable others skilled in the art to understand it more completely. It should be understood, however, that the invention is not limited solely to the particular examples given below.

EXAMPLE 1

2-[(β-Dimethylamino-ethyl)-amino]-4-(2′,6′-dichlorophenyl)-2-imidazoline hydrochloride by method A A mixture consisting of 6.0 gm (0.0202 mol) of 2-methylmercapto-4-(2′,6′-dichloro-phenyl)-2-imidazoline hydrochloride (m.p. 220° C) and 2.2 gm (0.025 mol) of N,N-dimethylamino-ethylenediamine was heated at 160° C for 30 minutes. The mixture was then allowed to cool, and the resulting glassy substance was dissolved in ethanol and then reprecipitated by addition of ether to the ethanolic solution. The precipitate was collected and repeatedly recrystallized from ethanol/ether, yielding 3.5 gm (51.5% of theory) of the pure, white crystalline compound of the formula

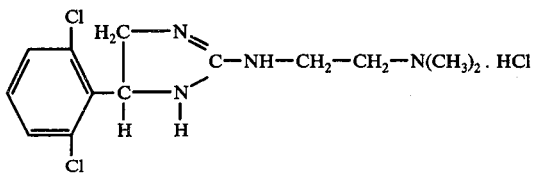

which had a melting point of 170° C.

EXAMPLE 2

2-(N′-methyl-piperazino)-4-(2′,4′-dichloro-phenyl)-2-imidazoline hydrochloride by method A A mixture consisting of 4.0 gm (0.0134 mol) of 2-methylmercapto-4-(2′,4′-dichloro-phenyl)-2-imidazoline hydrochloride and 1.35 gm (0.0135 mol) of N-methyl-piperazine was heated for 30 minutes at 130° C, whereby the initially molten mass solidified. The cooled solid mass was comminuted, dissolved in ethanol and reprecipitated from the solution by addition of ether. The precipitate was collected and repeatedly recrystallized from ethanol, yielding 1.1 gm (23.2% of theory) of the analytically pure, white crystalline compound of the formula

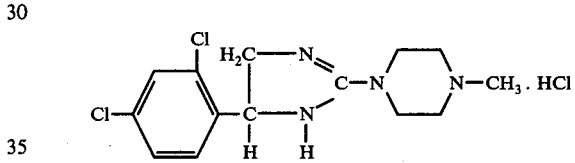

which had a melting point of 261° C.

EXAMPLE 3

2-[(β-Morpholino-ethyl)-amino]-4-(2′,6′-dichlorophenyl)-2-imidazoline hydrochloride by method A A mixture consisting of 6.0 gm (0.0202 mol) of 2-methylmercapto-4-(2′,6′-dichloro-phenyl)-2-imidazoline hydrochloride and 3.25 gm (0.025 mol) of N-(β-amino-ethyl)-morpholine was melted by heating it for 30 minutes at 150° C. Thereafter, while still hot, the molten mass was dissolved in ethanol and reprecipitated from solution by addition of ether. The precipitate, which solidified after some time, was collected and recrystallized from ethanol/acetone and, for further purification, briefly heated in boiling water in the presence of activated charcoal. The mixture was filtered, the filtrate was evaporated to dryness, and the residue was washed with acetone, yielding 3.0 gm (41.8% of theory) of the white crystalline compound of the formula

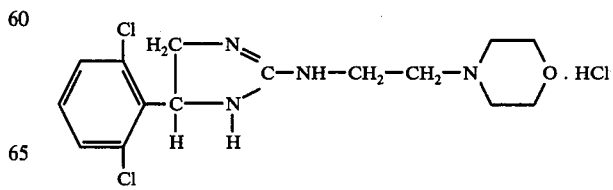

which had a melting point of 225° C.

EXAMPLE 4

2-(Furfuryl-amino)-4-(2',6'-dichloro-phenyl)-2-imidazoline hydrochloride by method A A mixture consisting fo 6.0 gm (0.0202 mol) of 2-methylmercapto-4-(2',6'-dichloro-phenyl)-2-imidazoline hydrochloride and 2.8 gm (0.029 mol) of furfurylamine was heated for 30 minutes at 140° C. The resulting dark-brown mass was dissolved in ethanol and then crystallized by addition of acetone and ether; for further purification, the crystallizate was again dissolved in ethanol and acetone, reprecipitated by addition of ether, and recrystallized from water, yielding 2.5 gm (35.7% of theory) of the yellow crystalline compound of the formula

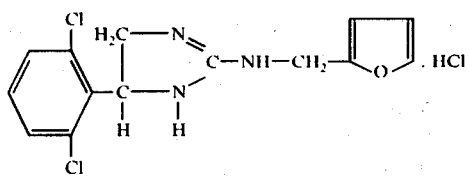

which had a melting point of 191° C.

EXAMPLE 5

2-Morpholino-4-(p-tolyl)-2-imidazoline oxalate by method A

A mixture consisting of 10 gm (0.0405 mol) of 2-methylmercapto-4-(p-tolyl)-2-imidazoline hydrochloride and 3.5 gm (0.0405 mol) of morpholine was heated for 45 minutes at 140° C. The resulting viscous mass was dissolved in water, and the aqueous solution was made alkaline with sodium hydroxide and then extracted with ether. The ethereal extract was dried with sodium sulfate and subsequently admixed with an ethereal solution of oxalic acid. The precipitate formed thereby was collected and recrystallized several times from ethanol, yielding the analytically pure compound of the formula

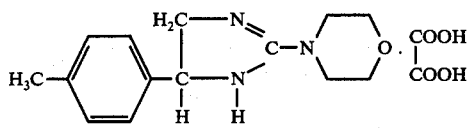

which had a melting point of 225° C.

EXAMPLE 6

2-[(β-Hydroxy-ethyl)-amino]-4-(2',6'-dichloro-phenyl)-2-imidazoline hydroiodide by method A 5.0 gm (0.0129 mol) of 2-methylmercapto-4-(2',6'-dichloro-phenyl)-2-imidazoline hydroiodide and 7.9 gm (0.13 mol) of ethanolamine were dissolved in 30 ml of ethanol, and the solution was heated in an autoclave for 3 hours at 130° C. Thereafter, the reaction solution was cooled and then admixed with ether, and the crystals precipitated thereby were collected, washed with acetone and recrystallized from ethanol/ether, yielding 1.5 gm (29% of theory) of the pure compound of the formula

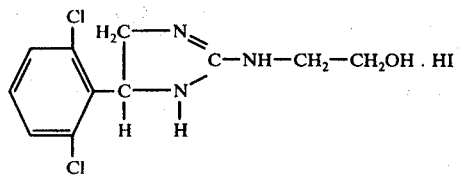

EXAMPLE 7

Using a procedure analogous to that described in Example 3, 2-piperidino-4-(2',6'-dichloro-phenyl)-2-imidazoline hydrochloride, m.p. 257° C, of the formula

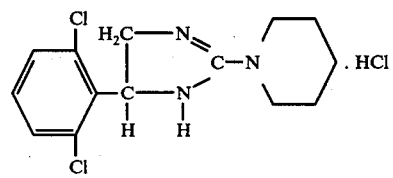

was prepared from 2-methylmercapto-4-(2',6'-dichlorophenyl)-2-imidazoline hydrochloride and piperidine.

EXAMPLE 8

Using a procedure analogous to that described in Example 1, 2-[(β-diethylamino-ethyl)-amino]-4-(2',6'-dichloro-phenyl)-2-imidazoline hydrochloride, m.p. 174° C, was prepared from 2-methylmercapto-4-(2',6'-dichloro-phenyl)-2-imidazoline hydrochloride and N,N-diethylamino-ethylenediamine.

EXAMPLE 9

Using a procedure analogous to that described in Example 3, 2-[(β-pyrrolidino-ethyl)-amino]-4-(2',6'-dichlorophenyl)-2-imidazoline hydrochloride, m.p. 208° C, of the formula

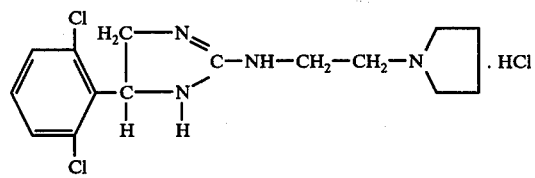

was prepared from 2-methylmercapto-4-(2',6'-dichloro-phenyl)-2-imidazoline hydrochloride and β-aminoethyl-pyrrolidine.

EXAMPLE 10

Using a procedure analogous to that described in Example 3, 2-morpholino-4-(2',6'-dichloro-phenyl)-2-imidazoline hydrochloride, m.p. 240° C, was prepared from 2-methylmercapto-4-(2',6'-dichloro-phenyl)-2-imidazoline hydrochloride and morpholine.

EXAMPLE 11

Using a procedure analogous to that described in Example 5, 2-[(N'-ethyl-3'-piperidyl)-amino]-4-(2'',6''-dichloro-phenyl)-2-imidazoline oxalate, m.p. 81° C, of the formula

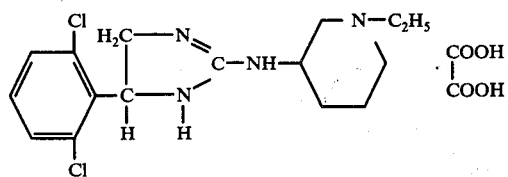

was prepared from 2-methylmercapto-4-(2',6'-dichloro-phenyl)-2-imidazoline hydrochloride and (N-ethyl-3-piperidyl)-amine.

EXAMPLE 12

Using a procedure analogous to that described in Example 5, 2-[(β-dimethylamino-ethyl)-amino]-4-(p-chlorophenyl)-2-imidazoline oxalate, m.p. 175° C, was prepared from 2-methylmercapto-4-(p-chloro-phenyl)-2-imidazoline hydrochloride and N,N-dimethyl-ethylenediamine.

EXAMPLE 13

Using a procedure analogous to that described in Example 5, 2(2',6'-dimethyl-morpholino)-4(p-chloro-phenyl)-2-imidazoline oxalate, m.p. 195° C, of the formula

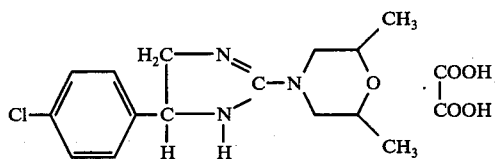

was prepared from 2-methylmercapto-4-(p-chloro-phenyl)-2-imidazoline hydrochloride and 2,6-dimethyl-morpholine.

EXAMPLE 14

Using a procedure analogous to that described in Example 5, 2-(N'-methyl-piperazino)-4-(p-chloro-phenyl)-2-imidazoline oxalate, m.p. 210° C, was prepared from 2-methylmercapto-4-(p-chloro-phenyl)-2-imidazoline hydrochloride and N-methyl-piperazine.

EXAMPLE 15

Using a procedure analogous to that described in Example 5, 2-[(β-dimethylamino-ethyl)-amino]-4-(p-bromophenyl)-2-imidazoline oxalate, m.p. 170° C, was prepared from 2-methylmercapto-4-(p-bromo-phenyl)-2-imidazoline hydrochloride and N,N-dimethyl-ethylenediamine.

EXAMPLE 16

Using a procedure analogous to that described in Example 5, 2-[(β-morpholino-ethyl)-amino]-4-(p-tolyl)-2-imidazoline oxalate, m.p. 132° C, was prepared from 2-methylmercapto-4-(p-tolyl)-2-imidazoline hydrochloride and N-(β-amino-ethyl)-morpholine.

EXAMPLE 17

Using a procedure analogous to that described in Example 5, 2-[(β-diethylamino-ethyl)-amino]-4-(p-tolyl)-2-imidazoline oxalate, m.p. 140° C, was prepared from 2-methylmercapto-4-(p-tolyl)-2-imidazoline hydrochloride and N,N-diethyl-ethylenediamine.

EXAMPLE 18

Using a procedure analogous to that described in Example 5, 2-methylamino-4-(2',6'-dichloro-phenyl)-2-imidazoline fumarate, m.p. 175° C, of the formula

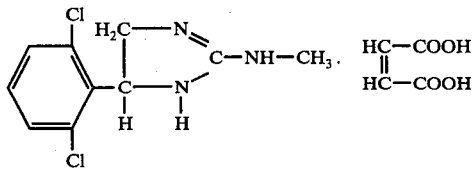

was prepared from 2-methylmercapto-4-(2',6'-dichloro-phenyl)-2-imidazoline hydrochloride, methylamine and ethereal fumaric acid.

EXAMPLE 19

Using a procedure analogous to that described in Example 5, 2-[(γ-morpholino-n-propyl)-amino]-4-(2',6'-dichloro-phenyl)-2-imidazoline dioxalate, m.p. 185° C, was prepared from 2-methylmercapto-4-(2',6'-dichloro-phenyl)-2-imidazoline hydrochloride and N-(γ-amino-n-propyl)-morpholine.

EXAMPLE 20

Using a procedure analogous to that described in Example 5, 2-[(γ-diethylamino-n-propyl)-amino]-4-(2',6'-dichloro-phenyl)-2-imidazoline dinitrate, m.p. 152° C, was prepared from 2-methylmercapto-4-(2',6'-dichloro-phenyl)-2-imidazoline hydrochloride, N,N-diethyl-propylenediamine and ethereal nitric acid.

EXAMPLE 21

Using a procedure analogous to that described in Example 5, 2-[(β-p-chlorophenyl-ethyl)-amino]-4-(2',6'-dichloro-phenyl)-2-imidazoline nitrate, m.p. 215° C, of the formula

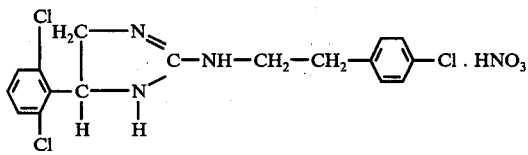

was prepared from 2-methylmercapto-4-(2',6'-dichloro-phenyl)-2-imidazoline hydrochloride, (β-p-chlorophenyl-ethyl)amine and ethereal nitric acid.

EXAMPLE 22

Using a procedure analogous to that described in Example 5, 2-[β-{N'-(2',6'-dimethyl-phenyl)-piperazino}ethyl-amino]-4-(2',6'-dichloro-phenyl)-2-imidazoline dioxalate, m.p. 228° C, of the formula

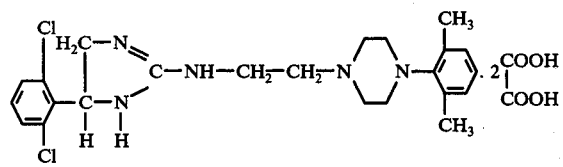

was prepared from 2-methylmercapto-4-(2',6'-dichloro-phenyl)-2-imidazoline hydrochloride and [β-{N'-(2,6-dimethyl-phenyl)-piperazino}-ethyl]-amine.

EXAMPLE 23

Using a procedure analogous to that described in Example 5, 2-[(γ-dimethylamino-α,β-dimethyl-n-propyl)-amino]-4-(2',6'-dichloro-phenyl)-2-imidazoline fumarate, m.p. 195° C, of the formula

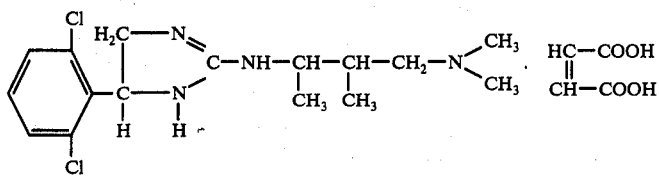

was prepared from 2-methylmercapto-4-(2',6'-dichloro-phenyl)-2-imidazoline hydrochloride and [γ(dimethylamino)-α,β-dimethyl-n-propyl]-amine.

EXAMPLE 24

Using a procedure analogous to that described in Example 5, 2-[(β-2',6'-dichlorophenyl-ethyl)-amino]-4-(2",6"-dichloro-phenyl)-2-imidazoline nitrate, m.p. 182° C, was prepared from 2-methylmercapto-4-(2',6'-dichloro-phenyl)-2-imidazoline hydrochloride, [β-(2,6-dichloro-phenyl)-ethyl]amine and ethereal nitric acid.

EXAMPLE 25

Using a procedure analogous to that described in Example 5, 2-[(β-phenyl-β-hydroxy-ethyl)-amino]-4-(2',6'-dichloro-phenyl)-2-imidazoline oxalate, m.p. 155° C, of the formula

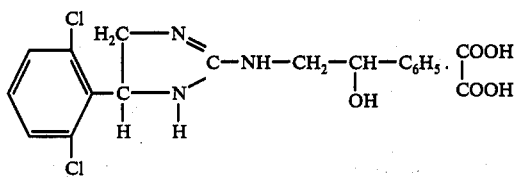

was prepared from 2-methylmercapto-4-(2',6'-dichloro-phenyl)-2-imidazoline hydrochloride and (β-phenyl-β-hydroxy-ethyl)amine.

EXAMPLE 26

2-Amino-3-methyl-4-(2',4'-dichloro-phenyl)-2-imidazoline hydrobromide by method B A solution of 27 gm of cyanogen bromide in 200 ml of absolute tetrahydrofuran was added dropwise over a period of 20 minutes to a solution of 56 gm (0.255 mol) of [β-(2,4-dichloro-phenyl)-β-methylamino-ethyl]-amine in a mixture of 200 ml of absolute tetrahydrofuran and 200 ml of ethanol at 10° C, while stirring. Thereafter, the reaction mixture was stirred for three hours at 20° C and then for 30 minutes at reflux temperature. Subsequently, the reaction mixture was allowed to cool, was then diluted with a mixture of ether and gasoline (1:1), and cooled to −15° C. The crystals precipitated thereby were collected by vacuum filtration and recrystallized from ethanol, yielding 43.7 gm (52.5% of theory) of the compound of the formula

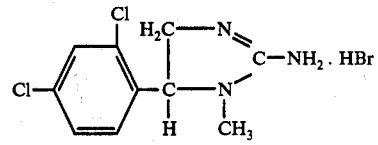

which had a melting point of 275°–278° C.

EXAMPLE 27

2-Amino-3-(β-morpholino-ethyl)-4-(2',6'-dichloro-phenyl)-2-imidazoline dioxalate by method B A solution of 6 gm (0.0565 mol) of cyanogen bromide in 80 ml of absolute tetrahydrofuran was added dropwise to a solution of 17.7 gm (0.0565 mol) of 2-(2',6'-dichloro-phenyl)-2-[(β-morpholino-ethyl)-amino]-ethylamine in a mixture of 80 ml of absolute tetrahydrofuran and 80 ml of ethanol at 10° C, and the resulting mixture was stirred for one hour at 20° C and then for 30 minutes at reflux temperature. Thereafter, the solvent was distilled off in vacuo, the residue was dissolved in water, and the aqueous solution was adjusted to pH 9 with sodium hydroxide and then extracted with ether. After addition of more strong sodium hydroxide to the aqueous phase it was extracted with chloroform, the organic extract was dried with sodium sulfate, and the dry extract was dried with sodium sulfate, and the dry extract solution was admixed with oxalic acid. The precipitate formed thereby was collected and recrystallized from isopropanol/methanol, yielding 12.5 gm (42.2% of theory) of the pure compound of the formula

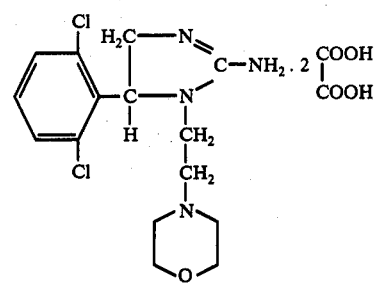

which had a melting point of 174° C.

EXAMPLE 28

2-(Furfuryl-amino)-3-methyl-4-(2',4'-dichloro-phenyl)-2imidazoline hydroiodide by method A A mixture consisting of 8.1 gm (0.02 mol) of 2-methylmercapto-3-methyl-4-(2',4'-dichloro-phenyl)-2-imidazoline hydroiodide (m.p. 170°–172° C) and 2.5 gm (0.028 mol) of furfurylamine was heated for 10 minutes at 110° C. Thereafter, the solidified reaction mixture was recrystallized several times from ethanol, yielding 6.1 gm (67.2% of theory) of the compound of the formula

[Structure: 2-(2',4'-dichlorophenyl)-3-methyl-imidazoline with C-NH-CH2-furan substituent] · HI which had a melting point of 186° C.

EXAMPLE 29

2-[(β-Diethylamino-ethyl)-amino]-3-methyl-4-(2',4'-dichlorophenyl)-2-imidazoline hydroiodide by method A A mixture consisting of 8.1 gm (0.02 mol) of 2-methylmercapto-3-methyl-4-(2',4'-dichloro-phenyl)-2imidazoline hydroiodide and 2.55 gm (0.022 mol) of N,N-diethylethylenediamine was heated for 20 minutes at 150° C. Thereafter, the reaction mixture was dissolved in ethanol, ether was added to the solution, and the precipitate formed thereby was collected and recrystallized from isopropanol/ether, yielding 4.2 gm (44.5% of theory) of the pure compound of the formula

[Structure: imidazoline derivative] C—NH—CH$_2$—CH$_2$—N(C$_2$H$_5$)$_2$ · HI which has a melting point of 144°–145° C.

EXAMPLE 30

2-Amino-3-ethyl-4-(2',6'-dichloro-phenyl)-2-imidazoline hydroiodide by method A

A mixture cosnsisting of 2 gm (0.0048 mol) of 2-methylmercapto-3-ethyl-4-(2',6'dichloro-phenyl)-2-imidazoline hydroiodide and 30 ml of concentrated ethanolic ammonia was heated for 3 hours at 130° C in a closed vessel. Thereafter, the reaction solution was evaporated to dryness, and the residue was recrystallized from isopentanol/ether and methanol/ether, yielding 1.3 gm (70% of theory) of the compound of the formula

[Structure: 2-amino-3-ethyl-4-(2',6'-dichlorophenyl)-2-imidazoline] · HI which had a melting point of 217° C.

EXAMPLE 31

2-Amino-3-methyl-4-(2',6'-dichloro-phenyl)-2-imidazoline sulfate by method C

A mixture consisting of 1.0 gm (0.0032 mol) of N-amidino-[β-(2,6-dichloro-phenyl)-β-methylamino-ethyl]-amine sulfate (m.p. 222° C) and 15 ml of hexamethylphosphoric triamide was heated for 1 hour at 160° C. After the reaction mixture had cooled, the crystalline substance was collected by vacuum filtration, washed with a little water and ether and recrystallized from ethanol, yielding 0.28 gm (30% of theory) of the compound of the formula

[Structure: 2-amino-3-methyl-4-(2',6'-dichlorophenyl)-2-imidazoline] · H$_2$SO$_4$ which had a decomposition point of about 323° C.

The starting compound, N-amidino-[β-(2,6-dichloro-phenyl)-β-methylamino-ethyl]-amine sulfate, was prepared as follows:

A mixture consisting of 21.9 gm (0.1 mol) of [β-(2,6-dichloro-phenyl)-β-methylamino-ethyl]-amine and 18 gm (0.1 mol) of S-methyl-isothiourea sulfate was heated for 20 minutes at 130° C. Thereafter, the solidified mass was extracted several times with hot ethanol, the extract solutions were combined, ether was added thereto, and the precipitate formed thereby was collected and recrystallized from ethanol, methanol and water. 3.7 gm of the pure product were obtained.

EXAMPLE 32

2-Methylamino-4-(2',6'-dichloro-phenyl)-2-imidazoline fumarate by method C

A mixture consisting of 2.5 gm of [2-(N,N'-dimethylguanidino)-2-(2',6'-dichloro-phenyl)-ethyl]-amine hydroiodide and 40 ml of hexamethylphosphoric triamide was heated for 6 hours at 220° C. After cooling, the reaction mixture was diluted with water, made alkaline with sodium hydroxide, and extracted with ether. The extract solution was dried and admixed with fumaric acid, and the precipitate formed thereby was collected and recrystallized from ethanol/ether, yielding the same compound as in Example 18, with a melting point of 173°–175° C.

The starting compound, [2-(N,N'-dimethylguanidino)-2-(2',6'-dichloro-phenyl)-ethyl]-amine hydroiodide, was prepared in the following manner:

A mixture consisting of 10.25 gm (0.05 mol) of 2,6-dichlorophenyl-ethylenediamine and 12.48 gm (0.05 mol) of N,N'-dimethyl-S-methyl-isothiourea hydroiodide was heated for 20 minutes at 130° C. The resulting molten mixture was dissolved in ethanol, the solution was admixed with ether, and the precipitate formed thereby was collected and recrystallized from pure ethanol. 2.5 gm (12.4% of theory) of the product, m.p. 176° C, were obtained.

EXAMPLE 33

Using a procedure analogous to that described in Example 32, 2-methylamino-3-methyl-4-(2',6'-dichlorophenyl)-2-imidazoline fumarate, m.p. 172° C, was prepared from N-symmetrical dimethylamidino-[β-(2', 6'-dichloro-phenyl)-β-methylamino-ethyl]-amine hydroiodide (m.p. 191° C).

The starting compound was obtained by reacting [β-(2,6-dichloro-phenyl)-β-methylamino-ethyl]-amine with S-methyl-N,N'-dimethyl-isothiourea hydroiodide.

EXAMPLE 34

2-Ethylamino-3-(β-diethylamino-ethyl)-4-(2',6'-dichlorophenyl)-2-imidazoline hydroiodide 17.1 gm (0.12 mol) of ethyl iodide were added to a solution of 16.5 gm (0.05 mol) of 2-amino-3-(β-diethylaminoethyl)-4-(2',6'-dichloro-phenyl)-2-imidazoline, and the mixture was heated for 3 hours at 70° C. Thereafter, the reaction solution was concentrated to about 20 ml by evaporation in vacuo, acetone and ether were added to the concentrate, and the precipitate formed thereby was collected, recrystallized several times from isopropanol, and washed with a little water and ether. 2.8 gm (11.6% of theory) of the pure product of the formula

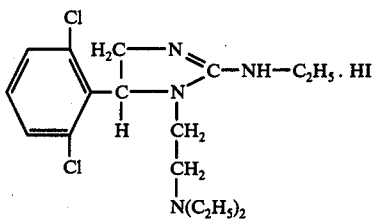

with a melting point of 193° C were obtained. The structure of the product was ascertained by means of NMR-spectra.

EXAMPLE 35

Using a procedure analogous to that described in Example 26, 2-amino-3-methyl-4-(p-chloro-phenyl)-2-imidazoline hydrobromide, m.p. 311° C, was prepared from [β-(p-chlorophenyl)-β-methylamino-ethyl]-amine and cyanogen bromide.

Its hydrochloride had a melting point of 331° C.

EXAMPLE 36

Using a procedure analogous to that described in Example 26, 2-amino-3-ethyl-4-(p-chloro-phenyl)-2-imidazoline hydrobromide, m.p. 202°-203° C, was prepared from [β-(p-chlorophenyl)-β-ethylamino-ethyl]-amine and cyanogen bromide.

EXAMPLE 37

Using a procedure analogous to that described in Example 26, 2-amino-3-furfuryl-4-(p-chloro-phenyl)-2-imidazoline hydrochloride, m.p. 257°-261° C, of the formula

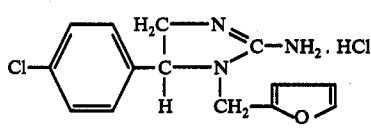

was prepared from [β-(p-chloro-phenyl)-β-(furfuryl-amino)-ethyl]-amine and cyanogen chloride.

EXAMPLE 38

Using a procedure analogous to that described in Example 26, 2-amino-3-ethyl-4-(2', 6'-dichloro-phenyl)-2-imidazoline hydrobromide, m.p. 219° C., was prepared from [β-(2,6-dichloro-phenyl)-β-ethlamino-ethyl]amine and cyanogen bromide.

EXAMPLE 39

Using a procedure analogous to that described in Example 26, 2-amino-3-(β-hydroxy-ethyl)-4-(2',6'-dichlorophenyl)-2-imidazoline hydrochloride, m.p. 235°-236° C., of the formula

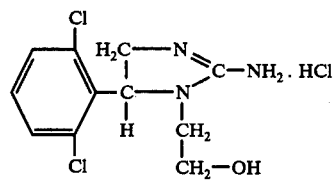

was prepared from [β(2,6-dichloro-phenyl)-β-ethanolaminoethyl]-amine and cyanogen chloride.

EXAMPLE 40

Using a procedure analogous to that described in Example 26, 2-amino-3-furfuryl-4-(2', 6'-dichloro-phenyl)-2-imidazoline hydrochloride, m.p. 229°-231° C., was prepared from [β-(2,6-dichloro-phenyl)-β-(furfuryl-amino)-ethyl]-amine and cyanogen chloride.

EXAMPLE 41

Using a procedure analogous to that described in Example 27, 2-amino-3-(β-diethylamino-ethyl)-4-(2', 6'-dichloro-phenyl)-2-imidazoline oxalate, m.p. 182° C., was prepared from [β-(2,6-dichloro-phenyl(-β-(2'-diethylaminoethyl)-ethyl]-amine, cyanogen bromide and oxalic acid.

EXAMPLE 42

Using a procedure analogous to that described in Example 28, 2-[(β-pyrrolidino-ethyl)-amino]-3-methyl-4-(2', 6'-dichloro-phenyl)-2-imidazoline hydrochloride, m.p.213°-214° C., was prepared from 2-methylmercapto-3-methyl-4-(2',6'-dichloro-phenyl)-2-imidazoline hydrochloride and (β-pyrrolidino-ethyl)-amine.

EXAMPLE 43

Using a procedure analogous to that described in Example 29, 2-methylmino-3-ethyl-4-(2',6'-dichloro-phenyl)-2-imidazoline hydroiodide, m.p. 200° C., was prepared from 2-methylmercapto-3-ethyl-4-(2',6'-dichloro-phenyl)-2-imidazoline hydroiodide and methylamine.

EXAMPLE 44

Using a procedure analogous to that described in Example 5, 2-[(β-diethylamino-ethyl)-amino]-3-methyl-4-(2', 6'-dichloro-phenyl)-2-imidazoline dioxalate, m.p. 155° C., was prepared from 2-methylmercapto-3-methyl-4-(2',6'-dichlorophenyl)-2-imidazoline hydrochloride and N,N-diethyl-ethylene diamine, followed by conversion of the hydrochloride into the dioxalate.

EXAMPLE 45

Using a procedure analogous to that described in Example 28, 2-(furfuryl-amino)-3-methyl-4-(2',6'-dichlorophenyl-2-imidazoline fumarate, m.p. 155° C., was prepared from 2-methylmercapto-3-methyl-4-(2',6'-dichloro-phenyl)-2-imidazoline fumarate and furfurylamine.

EXAMPLE 46

Using a procedure analogous to that described in Example 28, 2-(furfuryl-amino)-3-ethyl-4-(2',6'-dichlorophenyl)-2-imidazoline hydroiodide, m.p. 232° C., was prepared from 2-methylmercapto-3-ethyl-4-(2',6'-dichloro-phenyl)-2-imidazoline hydroiodide and furfurylamino.

EXAMPLE 47

Using a procedure analogous to that described in Example 5, 2-[(β-piperazino-ethyl)-amino]-3-methyl-4-(2',6'-dichloro-phenyl)-2-imidazoline trioxalate, m.p. 162° C., was prepared from 2-methylmercapto-3-methyl-4-(2',6'-dichlorophenyl)-2-imidazoline hydrochloride and (β-piperazino-ethyl)amine.

EXAMPLE 48

Using a procedure analogous to that described in Example 29, 2-[(β-diethylamino-ethyl)-amino]-3-ethyl-4-(2',6'-dichloro-phenyl)-2-imidazoline difumarate, an oil, was prepared from 2-methylmercapto-3-ethyl-4-(2',6'-dichlorophenyl)-2-imidazoline hydroiodide and N,N-diethyl-ethylenediamine, followed by conversion of the hydroiodide into the difumarate.

EXAMPLE 49

Using a procedure analogous to that described in Example 29, 2-[(β-p-chlorophenyl-ethyl)-amino]-3-methyl-4-(2',4'-dichloro-phenyl)-2-imidazoline hydroiodide, m.p. 174° C., was prepared from 2-methylmercapto-3-methyl-4-(2',4'-dichlorophenyl)-2-imidazoline hydroiodide and (β-p-chlorophenylethyl)-amine.

EXAMPLE 50

Using a procedure analogous to that described in Example 31, 2-amino-3-isopropyl-4-(chloro-phenyl)-2-imidazoline oxalate, m.p. 167° C., was prepared from N-amidino-[β-(p-chloro-phenyl)-β-isopropylamino-ethyl]-amine oxalate.

EXAMPLE 51

Using a procedure analogous to that described in Example 29, 2-[(β-p-chlorophenyl-ethyl)-amino]-3-methyl-4-(2',6'-dichloro-phenyl)-2-imidazoline hydroiodide, m.p. 220° C., was prepared from 2-methylmercapto-3-methyl-4-(2',6'-dichloro-phenyl)-2-imidazoline hydroiodide and (β-p-chlorophenyl-ethyl)-amine.

The compounds of the present invention, that is, those embraced by formula I and their non-toxic, pharmacologically acceptable acid addition salts, have useful pharmacodynamic properties. More particularly, they exhibit hypotensive, platelet aggregration inhibiting and antiarrhythmic activities in warm-blooded animals, such as rats, cats and dogs.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0008 to 1.34 mgm/kg body weight, preferably 0.0016 to 0.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 52

Tablets

The tablet composition is compounded from the following ingredients:

| | |
|---|---|
| 2-[(β-Dimethylamino-ethyl)-amino]-4-(2',6'-dichloro-phenyl)-2-imidazoline hydrochloride | 1 parts |
| Lactose | 65 |
| Corn starch | 125 |
| Sec. calcium phosphate | 40 |
| Soluble starch | 3 |
| Magnesium stearate | 2 |
| Colloidal silicic acid | 4 |
| Total | 240 parts |

Preparation

The imidazoline compound is intimately admixed with a substantial portion of each of the other ingredients except the soluble starch, the resulting mixture is moistened with an aqueous solution of the soluble starch, the moist mass is granulated through a screen, the granulate is dried and then admixed with the remainder of the inert ingredients, and the composition is compressed into 240 mgm-tablets in a conventional tablet making machine. Each tablet contains 1 mgm of the imidazoline compound and is an oral dosage unit composition with effective hypotensive action.

EXAMPLE 53

Hypodermic Solution

The solution is compounded from the following ingredients:

| | |
|---|---|
| 2-[(β-Morpholino-ethyl)-amino]-4-(2',6'-dichloro-phenyl)-2-imidazoline hydrochloride | 1 parts |
| Sodium chloride | 18 parts |
| Distilled water q.s.ad | 2000 parts by vol. |

Preparation

The imidazoline compound and the sodium chloride are dissolved in the distilled water, the solution is filtered until free from suspended particles, and the filtrate is filled into 2 cc - ampules in an atmosphere of nitrogen and under aseptic conditions. Each ampule contains 1 mgm of the imidazoline compound, and the contents are an injectable dosage unit composition with effective hypotensive action.

EXAMPLE 54

Drop Solution

The solution is compounded from the following ingredients:

| | |
|---|---|
| 2-Furfurylamino-4-(2',6'-dichloro-phenyl)-2-imidazoline hydrochloride | 20 parts |
| Methyl p-hydroxy-benzoate | 7 parts |
| Propyl p-hydroxy-benzoate | 3 parts |

| -continued | | |
|---|---|---|
| Demineralized water | q.s.ad | 100,000 parts by vol. |

Preparation

The ingredients are dissolved in a sufficient amount of the demineralized water, the solution is diluted to the indicated volume with additional demineralized water, the aqueous solution is filtered, and the filtrate is filled into 100 ml - bottles. 5 ml (about 20 drops) of the solution contain 1 mgm of the imidazoline compound and are an oral dosage unit composition with effective hypotensive action.

Analogous results are obtained when any one of the other imidazoline derivatives embraced by formula I or a non-toxic acid addition salt thereof is substituted for the particular imidazoline in Examples 52 through 54. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound selected from the group consisting of 2-[($\beta$-dimethylamino-ethyl)-amino]-4-(2',6'-dichloro-phenyl)-2-imidazoline and 2-furfurylamino-4-(2',6'-dichloro-phenyl)-2-imidazoline or a non-toxic, pharmacologically acceptable acid addition salt thereof.

2. A compound of claim 1 which is 2-[($\beta$-dimethylamino-ethyl)-amino]-4-(2',6'-dichloro-phenyl)-2-imidazoline or a non-toxic, pharmacologically acceptable acid addition salt thereof.

3. A compound of claim 1 which is 2-furfurylamino-4-(2',6'-dichloro-phenyl)-2-imidazoline or a non-toxic, pharmacologically acceptable acid addition salt thereof.

* * * * *